United States Patent [19]

Uno et al.

[11] Patent Number: 4,769,827
[45] Date of Patent: Sep. 6, 1988

[54] CAT SCANNER

[75] Inventors: Hideaki Uno; Hirofumi Yanagita, both of Tokyo, Japan

[73] Assignee: Yokogawa Medical Systems, Limited, Tokyo, Japan

[21] Appl. No.: 928,286

[22] PCT Filed: Feb. 26, 1986

[86] PCT No.: PCT/JP86/00094
§ 371 Date: Oct. 15, 1986
§ 102(e) Date: Oct. 15, 1986

[87] PCT Pub. No.: WO86/05084
PCT Pub. Date: Sep. 12, 1986

[30] Foreign Application Priority Data

Feb. 27, 1985 [JP] Japan ................................. 60-38249

[51] Int. Cl.$^4$ .............................................. A61B 6/02
[52] U.S. Cl. ...................................... 378/19; 378/114
[58] Field of Search ..................... 378/19.5, 4, 15, 11, 378/12, 20, 114, 901; 364/414; 250/385 R, 319

[56] References Cited

U.S. PATENT DOCUMENTS 4,041,315  8/1977  Hounsfield ............................ 378/11
4,211,926  7/1980  Nakaya et al. ....................... 378/20
4,484,340 11/1984  Yamaguchi et al. ................. 378/19

FOREIGN PATENT DOCUMENTS 2627433 12/1977 Fed. Rep. of Germany ........ 378/19
5438789 11/1986 Japan .

Primary Examiner—Carolyn E. Fields
Assistant Examiner—Joseph A. Hynds
Attorney, Agent, or Firm—Moonray Kojima

[57] ABSTRACT

The present invention provides a CAT (computerized axial tomography) scanner in which x-ray detector output currents are utilized efficiently and can be measured correctly, and which reconstructs an image of an object (11) under scrutiny without being materially affected by variations in the intensity of x-rays. The scanner has an x-ray tube (1) for continuously producing x-rays, which are directed toward an array (2) of x-ray detectors through the object (11). Capacitors ($3_1$–$3_{502}$) are charged by the output currents from the x-ray detectors ($2_1$–$2_{502}$) of the array. A control circuit controls first switches ($4_1$–$4_{502}$) and a second switch (6) in such a way that each capacitor initiates a cyclic process immediately after the previous capacitor is fully discharged. The cyclic process consists of a measurement, a resetting, and a charging. The control circuit also controls the order in which the cyclic operations are initiated, in such a way that the output currents from the x-ray detectors disposed near the center of the array and the output currents from reference x-ray detectors are measured at quite close instants.

1 Claim, 4 Drawing Sheets

CAT SCANNER

DESCRIPTION

1. Technical Field

The present invention relates to a CAT (computerized axial tomography) scanner using x-rays produced continuously and, more particularly, to a CAT scanner which is not materially affected by pulsating changes in the intensity of the used x-rays.

2. Background Art

The concept of the structure of a CAT scanner is illustrated in FIG. 1, where an x-ray tube 1 and an array 2 of x-ray detectors are rotatably disposed on opposite sides of an object 11 to be examined. The tube 1 emits x-rays in the form of a fan-shaped beam, most of which strikes x-ray detectors $2_2$–$2_{501}$ through the object 11. The x-rays are converted into electrical signals by the detectors. The x-rays in the vicinity of both ends of the fan-shaped beam hit reference x-ray detectors $A(2_1)$ and $B(2_{502})$ at both ends of the array 2 without passing through the object 11. The x-rays falling on the reference x-ray detectors are also converted into electrical signals. Capacitors $3_1$–$3_{502}$ are connected with the detectors $2_1$–$2_{502}$, respectively, and are charged by the output currents from the detectors. The voltages developed across the capacitors $3_1$–$3_{502}$ are applied via first switches $4_1$–$4_{502}$ and an amplifier 5 to an analog-to-digital converter 7, where they are converted to digital form. The digital signals delivered from the converter 7 are supplied to a computer 8, where the data is arithmetically processed in accordance with a given procedure to reconstruct an image of the object. The capacitors $3_1$–$3_{502}$ are discharged by closing a second switch 6 while the first switches $4_1$–$4_{502}$ are closed.

X-rays are produced from the x-ray tube 1 in the form of pulses at certain intervals. Each time one x-ray pulse hits each x-ray detector, the output current is measured. The measurements of the output currents from the detectors are made by controlling the sequence in which the first switches $4_1$–$4_{502}$ and the second switch 6 are selectively closed by a control circuit 9 as illustrated by the timing chart of FIG. 4. More specifically, the first switches $4_1$–$4_{502}$ are simultaneously closed at instant $t_1$ before each x-ray detector produces an output current I. Then, they are simultaneously opened at instant $t_2$. During this interval the second switch 6 is maintained closed and so the capacitors $3_1$–$3_{502}$ are discharged. The output current I rises at instant $t_3$ when an x-ray pulse falls on the detector, and drops at instant $t_4$. The second switch 6 is opened at instant $t_5$ after a certain period elapses since the output current I drops. During this interval the capacitors $3_1$–$3_{502}$ are charged by the output currents I from their respective x-ray detectors. Thereafter, the first switches $4_1$–$4_{502}$ are closed for a certain period in a given order to measure the voltages set up across the capacitors $3_1$–$3_{502}$. In particular, if the second switch 6 is opened at instant $t_5$, the switch $4_{249}$, for example, is then closed to measure the voltage developed across the capacitor $3_{249}$. Then, the switch $4_{249}$ is opened at instant $t_6$. Subsequently, the switch $4_{250}$ is closed to measure the voltage produced across the capacitor $3_{250}$. Subsequently, similar measurements are made of the voltages across the capacitors $3_{248}$, $3_{251}$, . . . , $3_1$, $3_{502}$. This sequence is shown in FIG. 5, where the numbers that the capacitors bear are shown against the numbers that the corresponding x-ray detectors bear.

In this measurement of the output current from each detector on which an x-ray pulse falls, the output current persists for a short time, compared with the period of the measurement. Therefore, in order to obtain a sufficient amount of output current, it is necessary to irradiate the patient with intense x-rays. This has tended to increase the absorbed dose.

In order to reduce the dose absorbed by the patient, continuous x-radiation may be contemplated. Specifically, the output current from each x-ray detector persists for a longer time, enhancing the efficiency of utilization of the detector output current. However, if the measurement sequence shown in FIG. 4 is used, accurate measurement cannot be made, because the period between the recharging of each capacitor and the beginning of measurement of the corresponding detector output current varies among different combinations of detectors and capacitors, and because the capacitors are recharged in different times.

If the scan sequence shown in FIG. 5 is utilized, a considerable period elapses between the instant at which the output currents from the x-ray detectors lying near the center of the detector array is measured and the instant at which the output currents from reference x-ray detectors are measured. During this period the x-ray tube voltage may pulsate, varying the intensity of the emitted x-rays. It is impossible to compensate for the variations in the intensity. Since the measured output currents from the substantially centrally located x-ray detectors are especially important for reconstruction of image, if the changes in the intensity of the x-rays are not compensated for, then the quality of the reconstructed image deteriorates.

DISCLOSURE OF THE INVENTION

It is the object of the present invention to provide a CAT scanner which utilizes detector output currents with high efficiency, is capable of measuring the detector output currents accurately, and reconstructs an image of the object under examination without being materially affected by changes in the intensity of x-rays.

In accordance with the invention, an x-ray tube (1) continuously produces x-rays which are directed to an x-ray detector array (2) via an object (11) to be examined. Capacitors ($3_1$–$3_{502}$) are charged by the output currents from the x-ray detectors ($2_1$–$2_{502}$). First switches ($4_1$–$4_{502}$) and a second switch (6) are controlled by a control circuit (9) in such a way that the voltage produced across each of the capacitors ($3_1$–$3_{502}$) is measured as soon as the previous capacitor is discharged. Then, the capacitor is discharged. Subsequently, it is charged. This process is repeated for every capacitor. The order in which individual processes are initiated is so controlled that the output currents from the x-ray detectors disposed near the center of the detector array are measured at instants very close to the instants at which the output currents from reference x-ray detectors are measured.

BEST MODE FOR CARRYING OUT THE INVENTION

Figure 1:
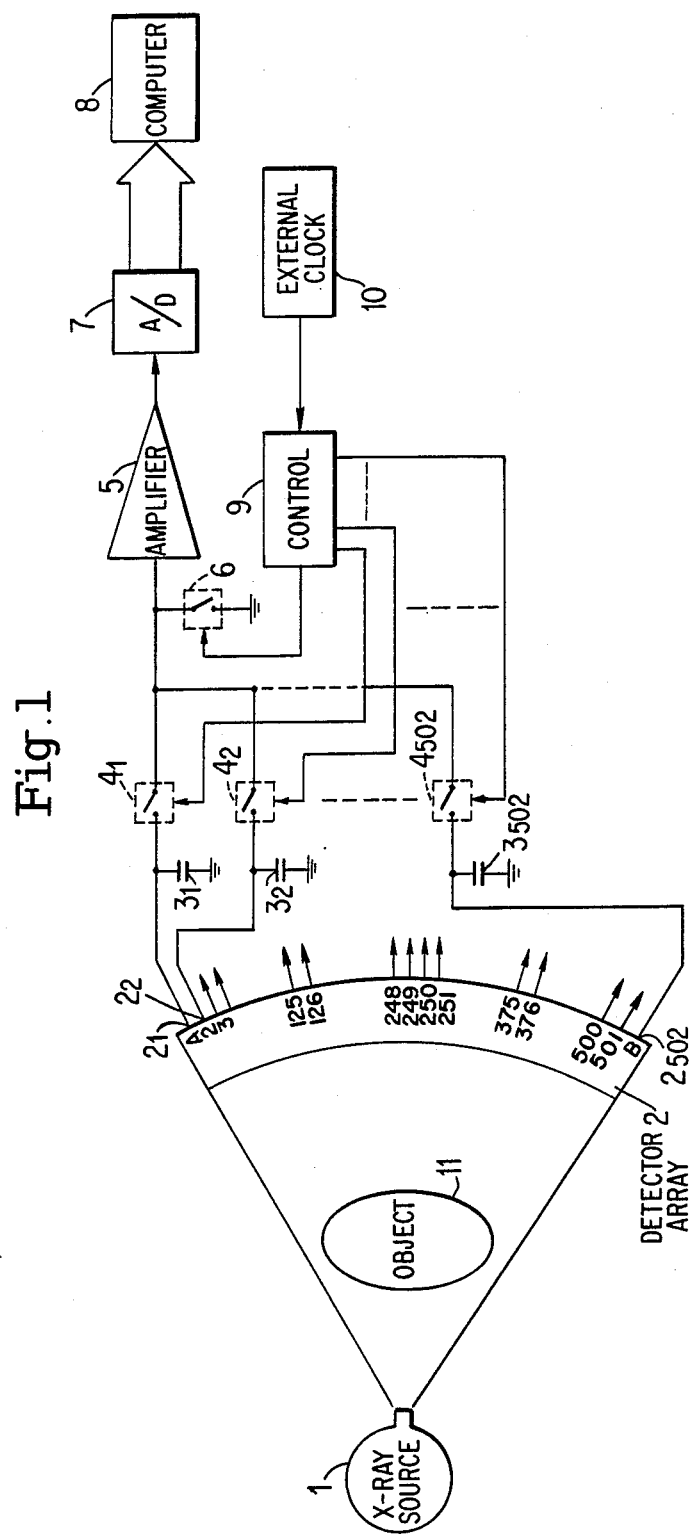
FIG. 1 is a schematic diagram of a CAT scanner according to the invention.
Figure 2:
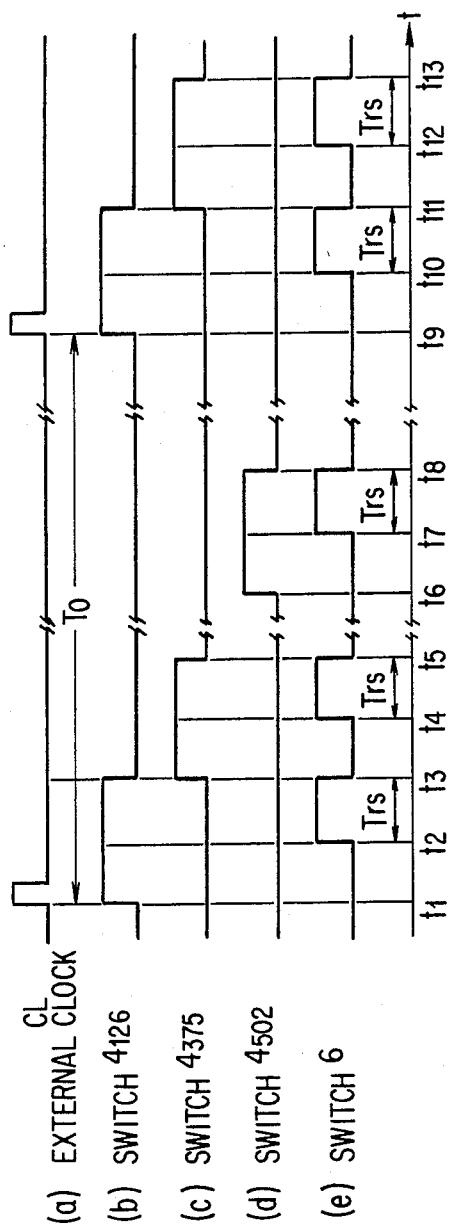
FIG. 2 is a timing chart for illustrating the operation of the scanner shown in FIG. 1.
Figure 4:
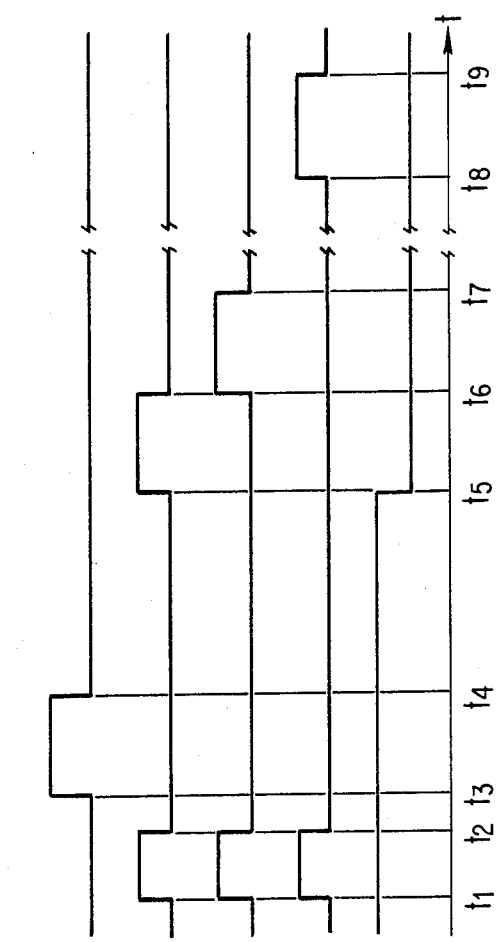
FIG. 4 is a timing chart for illustrating the operation of a conventional CAT scanner.

A CAT (computerized axial tomography) embodying the concept of the invention is now described also by referring to FIG. 1. X-ray tube 1 produces x-rays continuously. Control circuit 9 is used to make measurements in the sequence illustrated in FIG. 2. Clock pulses CL supplied from an external clock circuit 10 to the control circuit 9 are shown in FIG. 2(a). The operation of selected ones (e.g. $4_{126}$, $4_{375}$, $4_{502}$) of first switches $4_1$–$4_{502}$ is illustrated in FIG. 2 (b)–(d). The operation of second switch 6 is illustrated in FIG. 2(e).

The x-ray tube 1 produces x-rays in the form of a fan-shaped beam. Both ends of the fan-shaped beam hit x-ray detectors $2_1$ and $2_{502}$ without passing through the object 11 to be examined. The remaining portion of the fan-shaped beam passes through the object 11 and falls on the detectors $2_2$–$2_{501}$. Consequently, the detectors $2_1$–$2_{502}$ produce output currents in response to the continuously generated x-rays and serve as reference signals.

These output currents from the detectors are measured in the sequence described below under the control of the control circuit 9 that is clocked with the clock pulses CL supplied from the external clock circuit 10. First, one clock pulse CL is produced at instant $t_1$ to close the switch $4_{126}$. Then, the voltage developed across the capacitor $3_{126}$ is measured. Subsequently, the switch 6 is closed at instant $t_2$ while the switch $4_{126}$ is maintained closed, in order to discharge the capacitor $3_{126}$ which was used for the voltage measurement. The switches $4_{126}$ and 6 are opened at instant $t_3$ so that the capacitor $3_{126}$ is charged by the output current from the corresponding detector. The capacitor $3_{126}$ is kept charged until the next clock pulse CL is produced and the preparations for the next measurement are complete at instant $t_9$.

After the switch $4_{126}$ is opened, the switch $4_{375}$ is closed to measure the voltage produced across the capacitor $3_{375}$. After the completion of this measurement, the switch 6 is also closed at instant $t_4$ to discharge the capacitor $3_{375}$. Thereafter, the switches $4_{375}$ and 6 are opened so that the capacitor $3_{375}$ is charged by the detector output current.

Figure 3:
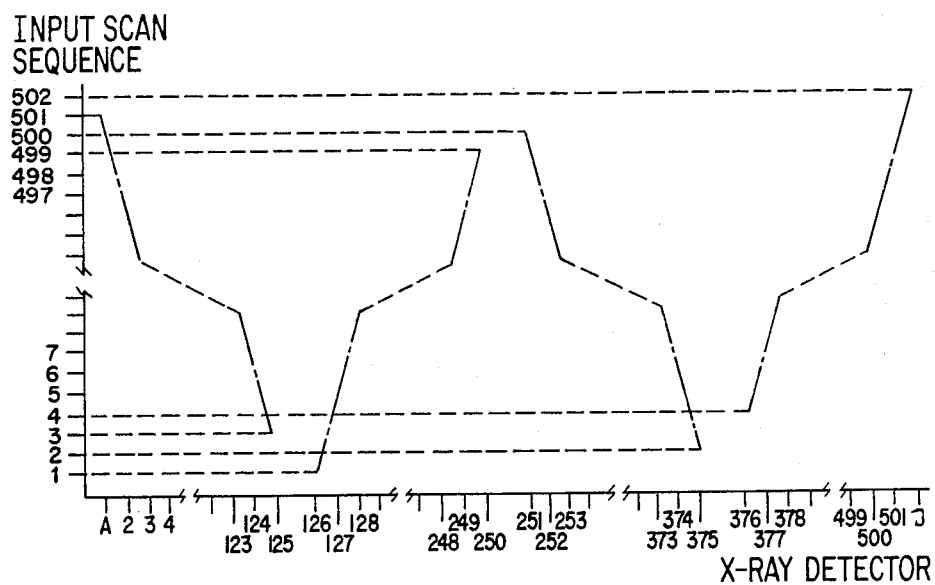
FIG. 3 is a diagram for illustrating the sequence of measurements made as illustrated in FIG. 2.
Figure 5:
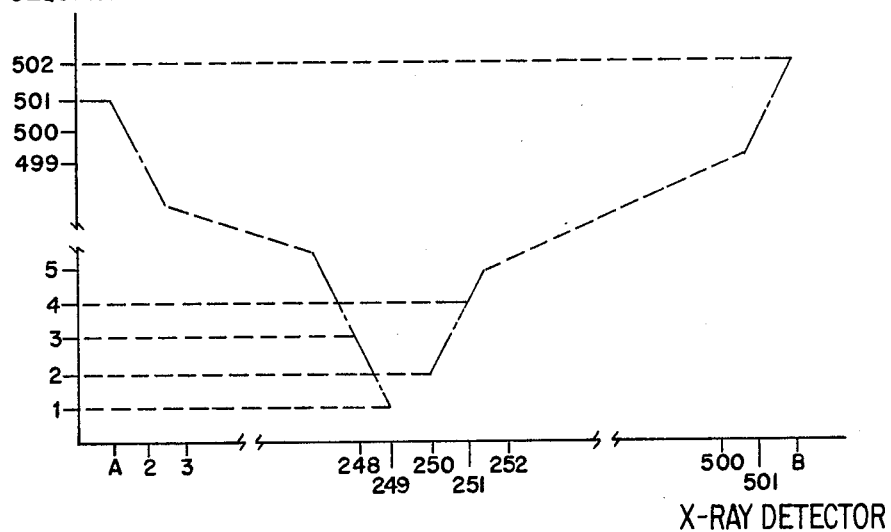
FIG. 5 is a diagram for illustrating the sequence of measurements made as illustrated in FIG. 4.

Subsequently, the first switches are controlled in the same manner using the capacitors $3_{125}$, $3_{376}$, ..., $3_{250}$, ..., $3_{501}$, and $3_{502}$ in this order. Each time each of these capacitors is employed, the second switch 6 is actuated in the same manner. This sequence of operations is illustrated in FIG. 3, where the numbers that the capacitors bear are shown against the numbers that the x-ray detectors bear.

This series of operations is repeated with the period $T_0$ of the external clock pulses CL. Accordingly, each of the capacitors $3_1$–$3_{502}$ is charged for a certain period of $T_0$–$T_{rs}$, where $T_{rs}$ is the period during which the switch 6 is closed for discharging. Hence, $T_{rs}$ can be called a dead time, and is appropriately set, taking account of the measuring accuracy and the time taken for each capacitor to discharge. In this case, the efficiency of utilization of the input current is defined as $(T_0-T_{rs})/T_0$. Since the closure time $T_{rs}$ can be made considerably shorter than the period $T_0$, it is possible to enhance the efficiency of utilization of the input current. Thus, every capacitor can be charged in the same time. Therefore, the output currents which are produced from the detectors in response to the continuously produced x-rays can be measured correctly. Also, since the utilization efficiency of the input current can be made high, it is possible to lower the intensity of the emitted x-rays. This leads to a reduction in the dose absorbed by the irradiated patient.

Referring again to FIG. 3, two positions which are a certain distance (=the length of the detector array 14) distant from both ends of the array 2 are used as starting points. Selection order paths extending from the starting points to the ends of the array are established. Also, selection order paths extending from the starting points to the center of the array are established. These four paths are selected in a given order. Also, detectors are selected in a certain sequence determined for each path. After the output currents from the x-ray detectors $2_{250}$ and $2_{251}$ disposed close to the center of the array are measured, the output currents from reference x-ray detectors A($2_1$) and B($2_{502}$) are measured. During these successive measurements, changes in the intensity of the emitted x-rays due to variations in the x-ray tube voltage are negligible. Therefore, it is possible to correctly find the reference value of the intensity of the x-rays that cause the detectors $2_{250}$ and $2_{251}$ lying near the center of the array to produce output currents. Consequently, high-quality tomograms can be obtained by making use of the reference value. Furthermore, it is possible to measure the output currents from adjacent x-ray detectors at instants that are rendered as closest to each other as possible.

It should be understood that the measurements of the output currents from x-ray detectors in accordance with the invention are made possible when the period of the external clock pulses is longer than the sum of the time required for the measurements using all the capacitors and the time taken to discharge the capacitors. Therefore, the period of the external clock pulses is restricted by this sum. When it is desired to shorten the period of the external clock pulses, i.e., to increase the rate at which measurements are made, the capacitors are divided into plural groups. A measuring circuit including an amplifier and an analog-to-digital converter is disposed for each group of capacitors. These groups are operated in parallel.

In the above example, two reference x-ray detectors A and B are provided. It is also possible to provide more reference x-ray detectors. In this case, during each single measurement, the output currents from these reference detectors may be measured several times. The output currents from the non-reference detectors may be compensated for, using the output currents from the reference detectors which are measured at close instants.

While the best mode for carrying out the present invention has been described, it should be understood by those skilled in the art that various changes and modifications may be made without departing from the spirit and scope of the invention which are delineated by the following claim.

I claim:
1. In a CAT scanner comprising
an x-ray source for producing x-rays in the form of a fan-shaped beam;
an array of x-ray detectors, including reference x-ray detectors upon which x-rays not transmitted through an object to be examined falls, the array and the x-ray source being disposed on opposite sides of the object;

a mechanism for rotating the x-ray source and the array of x-ray detectors while maintaining their respective positional relationship;

a plurality of capacitors connected to respective x-ray detectors of the array, the capacitors being charged by output currents from respective x-ray detectors;

a plurality of first switch means connected to respective capacitors;

means connected to said first switch means for measuring voltages developed across said capacitors;

a second switch means connected to said capacitors for enabling discharge of said capacitors; and control means for controlling the switching of said plurality of said first switch means and said second switch means to cause the voltage across selected capacitors to be selectively measured by said measuring means; the improvement comprising said x-ray source produces and applies to said object and to said reference detector directly continuous x-rays;

said control means is connected to and controls said plurality of first switch means and said second switch means and comprises a clock source, and causes the following sequence of operations:

causes all of said capacitors to be charged;

responsive to a clock pulse from said clock source causes closing of a selected one of said first switch means;

causes said means for measuring to measure the voltage across a selected capacitor connected to the closed selected first switch means;

causes said second switch to close while the selected first switch means is still closed, so as to discharge said selected capacitor;

causes opening of both the second switch means and the selected first switch means so as to charge the selected capacitor;

causes the selected capacitor to remain charged until the foregoing operations are repeated; and repeating the foregoing sequence of operations to selectively measure in any desired order all of said detectors including said reference detectors.

* * * * *